United States Patent [19]

Ohtsuka et al.

[11] Patent Number: 5,750,879

[45] Date of Patent: May 12, 1998

[54] STICK-SLIP DETECTION METHOD AND APPARATUS

[75] Inventors: Akira Ohtsuka; Chosei Kaseda, both of Tokyo, Japan

[73] Assignee: Yamatake-Honeywell Co., Ltd., Japan

[21] Appl. No.: 864,242

[22] Filed: May 28, 1997

[30] Foreign Application Priority Data

May 31, 1996 [JP] Japan ................................. 8-138258
Feb. 27, 1997 [JP] Japan ................................. 9-043347

[51] Int. Cl.$^6$ .................................................. G01N 19/04
[52] U.S. Cl. ...................................... 73/9; 73/865.9
[58] Field of Search ...................... 73/1.79, 7, 9, 11.09, 73/865.3, 865.9; 55/270, 274

[56] References Cited

U.S. PATENT DOCUMENTS 4,939,922  7/1990  Smalley et al. ............................. 73/9
5,542,281  8/1996  Lee et al. ................................... 73/9

OTHER PUBLICATIONS

Valve Technology pp. 12–17 (May, 1991).

*Primary Examiner*—Ronald L. Biegel
*Assistant Examiner*—Eric S. McCall
*Attorney, Agent, or Firm*—Blakely Sokoloff Taylor & Zafman

[57] ABSTRACT

In a stick-slip detection method, the displacement of a movable member having a slidable contact portion is detected. A first quantity of state is calculated on the basis of the detected displacement of the movable member. A second quantity of state, which can be estimated from the first quantity of state, is calculated on the basis of the detected displacement of the movable member. An estimated quantity of state is calculated by estimating a second quantity of state from the calculated first quantity of state by using the relationship between the first and second predetermined quantities of state which are obtained from the displacement of the movable member in a normal sliding state. The calculated second quantity of state is compared with the estimated quantity of state to determine an abnormal sliding operation of the movable member on the basis of the comparison result. A stick-slip detection apparatus is also disclosed.

14 Claims, 7 Drawing Sheets

STICK-SLIP DETECTION METHOD AND APPARATUS

BACKGROUND OF THE INVENTION

The present invention relates to a stick-slip detection method and apparatus for detecting stick-slip in the operation of a device having a slidable surface with a frictional contact portion, such as a control valve or a gas governor to perform fault diagnosis therefor.

Figure 10:
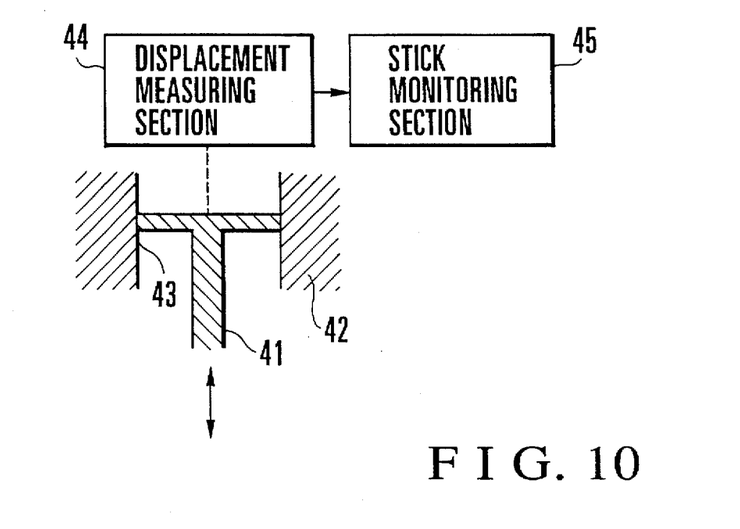
FIG. 10 is a view showing the arrangement of a conventional stick-slip detection apparatus for detecting the stick-slip of a piston having a slidable contact portion.

Fault diagnosis for a control valve or a gas governor can be performed by detecting the stick-slip of the slidable portion of such a device. For example, as shown in FIG. 10, stick-slip is caused depending on the state of a slidable contact portion 43 between a piston 41 and a cylinder 42. For example, this stick-slip is caused when a foreign substance adheres to the slidable contact portion 43. Stick-slip can therefore be detected by measuring the displacement of the piston 41 with a displacement measuring section 44 and monitoring the state of the displacement with a stick monitoring section 45.

Figure 11:
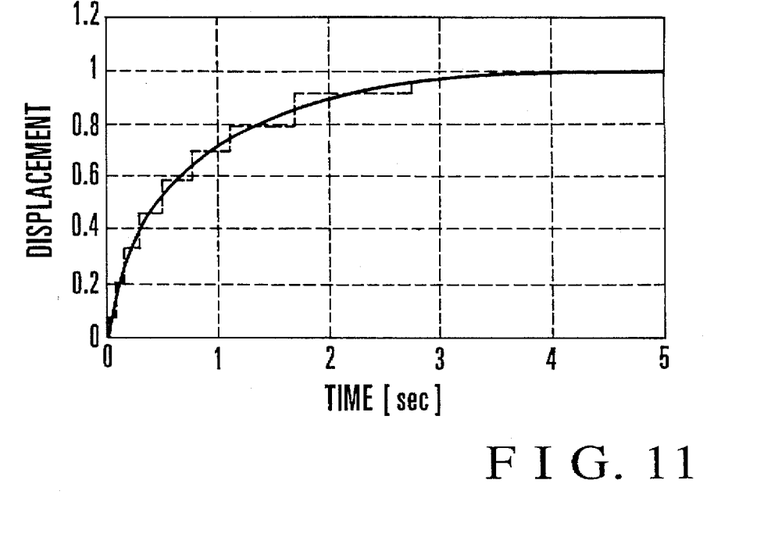
FIG. 11 is a graph showing a state in which stick-slip has occurred.

First of all, the state of the displacement of the piston 41 is detected by the displacement measuring section 44 while a driving input is applied to the piston 41. If the displacement undergoes no change for a predetermined period of time while the driving input is applied to the piston 41, the stick monitoring section 45 determines that stick-slip has occurred. FIG. 11 shows the displacement of the slidable portion of a control valve, measured by the displacement measuring section 44, as a function of time. Referring to FIG. 11, the solid curve indicates a normal state; and the dotted curve, a state in which stick-slip has occurred. As shown in FIG. 11, in the event of stick-slip, the displacement of the slidable portion does not continuously change with time.

The operation state of a system is monitored in this manner while a driving input is applied thereto. When the stick monitoring section 45 detects that the system does not operate for a predetermined period of time, as indicated by the dotted curve in FIG. 11, the occurrence of stick-slip can be detected.

However, the above conventional stick-slip detection technique is not based on analysis of the cause and phenomenon of stick-slip. For this reason, the conventional technique cannot detect the occurrence of stick-slip (frictional vibration) depending on the operating conditions for objects which slide on each other. There is no clear explanation about the difference between a case in which stick-slip cannot be detected and a case in which stick-slip can be detected.

Stick-slip in a given system corresponds to a state in which the system stops at short intervals. In practice, in the event of stick-slip, the sticking time changes as a function of parameters for a mechanism which causes stick-slip and an operating input, and hence the inoperative time varies. For this reason, it is difficult to set a uniform sticking time. Even if monitoring is performed with a fixed inoperative time, stick-slip cannot be reliably detected, as described above.

As indicated by the dotted curve in FIG. 11, in general, there is no possibility in the normal operation that a machine's response clearly indicating stick-slip will be generated. If, however, stick-slip does not occur to the degree shown in FIG. 11, it is difficult to detect stick-slip.

SUMMARY OF THE INVENTION

It is an object of the present invention to provide a stick-slip detection method and apparatus which can express the difference between a state in which stick-slip is caused and a normal state in quantity.

In order to achieve the above object, according to the present invention, there is provided a stick-slip detection method comprising the steps of detecting a displacement of a movable member having a slidable contact portion, calculating a first quantity of state on the basis of the detected displacement of the movable member, calculating a second quantity of state, which can be estimated from the first quantity of state, on the basis of the detected displacement of the movable member, calculating an estimated quantity of state by estimating a second quantity of state from the calculated first quantity of state by using the relationship between first and second predetermined quantities of state which are obtained from a displacement of the movable member in a normal sliding state, and comparing the calculated second quantity of state with the estimated quantity of state, and determining an abnormal sliding operation of the movable member on the basis of the comparison result.

DESCRIPTION OF THE PREFERRED EMBODIMENTS

The present invention will be described in detail below with reference to the accompanying drawings.

First Embodiment

Figure 1A:
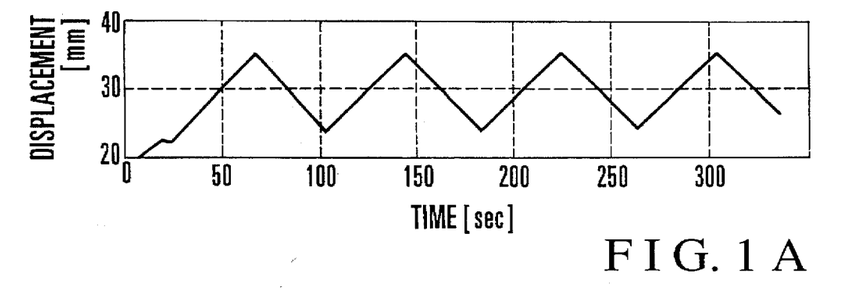
FIG. 1A is a graph showing a state in which no stick-slip has occurred.

The first embodiment will be briefly described first. When the displacement of a movable member having a slidable contact portion, which changes with time, is measured, characteristic curves like those shown in FIGS. 1A and 1B can be obtained. FIG. 1A shows a normal state; and FIG. 1B, a state in which stick-slip has occurred.

Figure 1B:
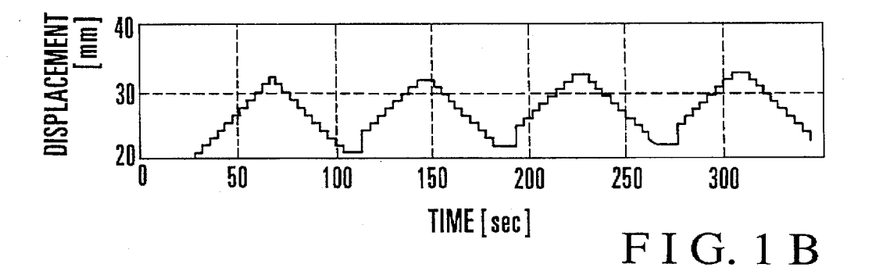
FIG. 1B is a graph showing a state in which stick-slip has occurred.

As shown in FIG. 1B, in the event of stick-slip, high-frequency components appear in a signal for indicating the displacement of the movable member. If, therefore, the occurrence of the high-frequency components can be detected by analyzing the signal for indicating the displacement of the movable member by Fourier transform, the occurrence of stick-slip can be determined.

In this case, the first order differentials of the displacement at given time t can be given by equation (1). Similarly, the second order differentials of the displacement at time t are given by equation (2). Note that equations (1) and (2) are expressed in the complex form, in which a represents the amplitude; $\omega$, the angular frequency; and j, the imaginary unit.

$$\dot{x}_t = \int_{-\infty}^{\infty} a_\omega e^{j\omega t} d\omega \tag{1}$$

$$\ddot{x}_t = j \int_{-\infty}^{\infty} a_\omega e^{j\omega t} d\omega \tag{2}$$

According to the above equations, known Parseval's equations (3) and (4) can be established:

$$\int_{\tau-T}^{\tau} \dot{x}_t^2 dt = \int_{-\infty}^{\infty} |a_\omega|^2 d\omega \tag{3}$$

$$\int_{\tau-T}^{\tau} \ddot{x}_t^2 dt = \int_{-\infty}^{\infty} |a_\Omega|^2 \omega^2 d\omega \tag{4}$$

The relationship between the first and second order differential values of the displacement can therefore be expressed by equation (5):

$$\frac{\ddot{x}_\tau}{\dot{x}_\tau} = \frac{\int_{\tau-T}^{\tau} \ddot{x}_t^2 dt}{\int_{\tau-T}^{\tau} \dot{x}_t^2 dt} = \frac{\int |a_\omega|^2 \omega^2 d\omega}{\int |a_\omega|^2 d\omega} = \frac{\int \alpha_\omega W dW}{\int \alpha_\omega dW} \tag{5}$$

where $|a_\omega|^2 = \alpha_\omega$ is the power spectrum of the first order differential signal of the displacement, and $\omega^2 = W$.

According to equation (5), the value obtained by dividing a second order differential value of the displacement by a first order differential value corresponds to an equilibrium point of the power spectrum of a first order differential signal of the displacement with respect to an axis W. That is, when a change in the relationship between the second and first order differential values of the displacement is obtained, a change in the above equilibrium point is obtained.

When stick-slip occurs, high-frequency components appear in the detected displacement signal, as a result, the equilibrium point changes. When, therefore, a change in the relationship between the second and first order differential values of the displacement is obtained, the occurrence of stick-slip can be detected.

Stick-slip detection according to the present invention will be described below.

Figure 2:
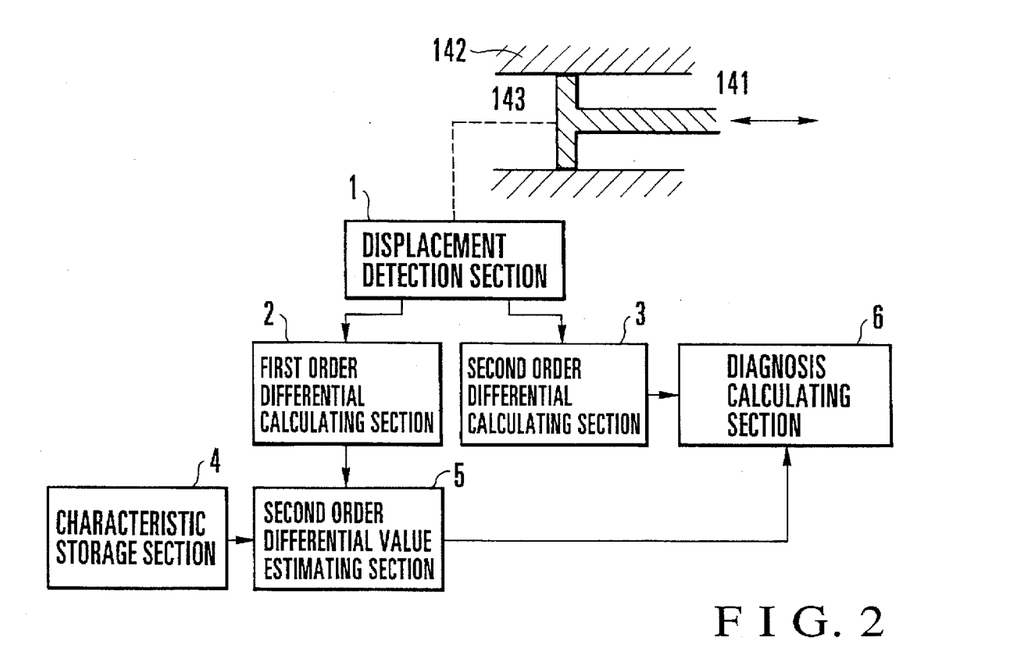
FIG. 2 is a block diagram showing the arrangement of a stick-slip detection apparatus according to the first and second embodiments of the present invention.

FIG. 2 shows the arrangement of a stick-slip detection apparatus according to the first embodiment of the present invention. Referring to FIG. 2, reference numeral 142 denotes a cylinder; 141, a piston as a movable member having a slidable contact portion 143 which is in slidable contact with the inner wall of the cylinder 142; 1, a displacement detecting section for measuring the displacement of the piston 141; 2, a first order differential calculating section for calculating the first order differentials of the detected displacement, and 3, a second order differential calculating section for calculating the second order differentials of the detected displacement.

Reference numeral 4 denotes a characteristic storage section in which the relationship (characteristic expression) between the first and second order differential values in a normal sliding state, obtained in advance, are stored; 5, a second order differential value estimating section for calculating an estimated second order differential value from a first order differential value calculated by the first order differential calculating section 2 by using the characteristic expression stored in the characteristic storage section 4; and 6, a diagnosis calculating section for comparing the estimated second order differential value calculated by the second order differential value estimating section 5 with the actual second order differential value calculated by the second order differential calculating section 3, and obtaining the degree of the difference.

First of all, the first order differential calculating section 2 obtains the first order differential values of a displacement signal obtained by measuring a displacement x of the piston 141 as a square sum in a time T, as indicated by equation (6):

$$\bar{\dot{x}} = \int_{\tau-T}^{\tau} \dot{x}_t^2 dt \tag{6}$$

where $\dot{x}$ is the first order differential value at time t.

The second order differential calculating section 3 obtains the second order differential values of the displacement signal as a square sum in the time T, as indicated by equation (7):

$$\bar{\ddot{x}} = \int_{\tau-T}^{\tau} \ddot{x}_t^2 dt \tag{7}$$

where $\ddot{x}$ is the second order differential value at time t.

The characteristic storage section 4 stores a characteristic expression obtained by a linear approximation with two constants A and B, like equation (8) as the simplest expression, as the relationship (characteristic expression) between the first and second order differentials of a displacement signal in a normal sliding state.

$$\ddot{X} = A * \dot{X} + B \tag{8}$$

The second order differential value estimating section 5 estimates a second order differential value from the first order differential value, obtained from the measurement value, by using equation (8) as the characteristic expression. The diagnosis calculating section 6 obtains the difference between the estimated second order differential value and the actual second order differential value by using equation (9):

$$E_\tau = \ddot{X}_\tau - (A * \dot{X}_\tau + B) \tag{9}$$

As described above, according to the first embodiment, an estimated second order differential value is obtained on the basis of a first order differential value of a displacement signal, and the estimated second order differential value is compared with the actual second order differential value obtained from the displacement of the piston 141. If a difference $E\tau$ between the two values is larger than a predetermined value, it is determined that stick-slip has occurred. In other words, to focus attention on the difference $E\tau$ between the estimated second order differential value and the actual second order differential value obtained from the displacement of the object is to focus attention on a change in the relationship between the second order differential value of the displacement and the first order differential value described above.

In the first embodiment described above, a second order differential value is estimated. However, the present invention is not limited to this. For example, a first order differential value may be estimated from a second order differential value, and the estimated first order differential value may be compared with the actual first order differential value obtained from the displacement of the object.

Second Embodiment

In the first embodiment, the first and second order differential values of a displacement signal are obtained by using equations (6) and (7). However, these values may be obtained by using equations (10) and (11):

$$\bar{\dot{x}} = \int_{\tau-T}^{\tau} |x_t| dt \quad (10)$$

$$\bar{\ddot{x}} = \int_{\tau-T}^{\tau} |\ddot{x}_t| dt \quad (11)$$

Third Embodiment

In the first and second embodiments described above, the obtained displacement signal is an analog signal. A case in which a displacement signal is a digital signal will be described below. In the following embodiment, a displacement of the piston 141 in FIG. 2 is detected by a displacement detecting section.

Figure 3:
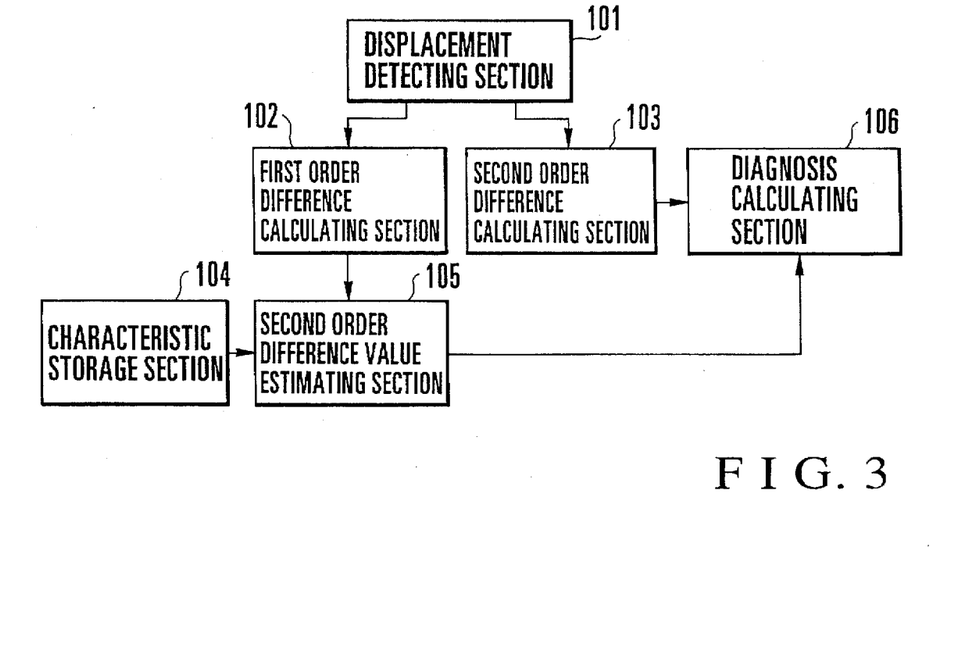
FIG. 3 is a block diagram showing the arrangement of a stick-slip detection apparatus according to the third embodiment of the present invention.

FIG. 3 shows the arrangement of a stick-slip detection apparatus according to the third embodiment of the present invention. In the first embodiment described above, as indicated by equations (6) and (7), first and second order differential values are obtained from the displacement signal obtained by differentiating an obtained analog displacement signal.

However, as shown in FIG. 3, when the displacement signal obtained by a displacement detecting section 101 is a digital signal, first and second order difference calculating sections 102 and 103 calculate first and second order difference values corresponding to first and second order differential values by using equations (12) and (13):

$$\overline{\delta x_\tau} = \sum_{t=\tau-t}^{\tau} (\delta x_t)^2 \quad (12)$$

$$\overline{\delta^2 x_\tau} = \sum_{t=\tau-t}^{\tau} (\delta^2 x_t)^2 \quad (13)$$

where $\delta x$ is the difference between the values x in $\Delta t$, which is obtained by equation (14):

$$\delta X_t = X_{t+\Delta t} - X_t \quad (14)$$

In the third embodiment, the characteristic expression stored in a characteristic storage section 104, which corresponds to equation (8) used in the first embodiment, is equation (15):

$$\overline{\delta^2 X_\tau} = A * \overline{\delta X_\tau} + B \quad (15)$$

A second order difference value estimating section 105 calculates an estimated second order difference value from a first order difference value obtained by equation (12) according to equation (15). The second order difference calculating section 103 calculates a second order difference value from the actual measurement value by using equation (13). A diagnosis calculating section 106 then obtains a difference $E\tau$ between the calculated second order difference value and the estimated second order difference value. If, for example, the difference $E\tau$ is larger than a predetermined value, the diagnosis calculating section 106 determines that stick-slip has occurred.

In the third embodiment as well, an estimated first order difference value may be inversely calculated from the second order difference value, obtained by equation (13), by using equation (15), and the inversely calculated estimated first order difference value may be compared with an actual first order difference value obtained by equation (12).

Fourth Embodiment

In the third embodiment, square sums are respectively obtained according to equations (12) and (13). However, the present invention is not limited to this. For example, the sum of first order difference values and the sum of second order difference values may be calculated by using equations (16) and (17), respectively:

$$\overline{\delta x_\tau} = \sum_{t=\tau-T}^{\tau} |\delta x_t| \quad (16)$$

$$\overline{\delta^2 x_\tau} = \sum_{t=\tau-T}^{\tau} |\delta^2 x_t| \quad (17)$$

In this case, an estimated second order difference value is calculated from the value obtained by equation (16) by using equation (15). A second order difference value is calculated from the actual measurement value by using equation (17). A difference $E\tau$ between the second order difference value and the estimated second order difference value is obtained. If the difference $E\tau$ is larger than a predetermined value, it is determined that stick-slip has occurred.

Figure 4:
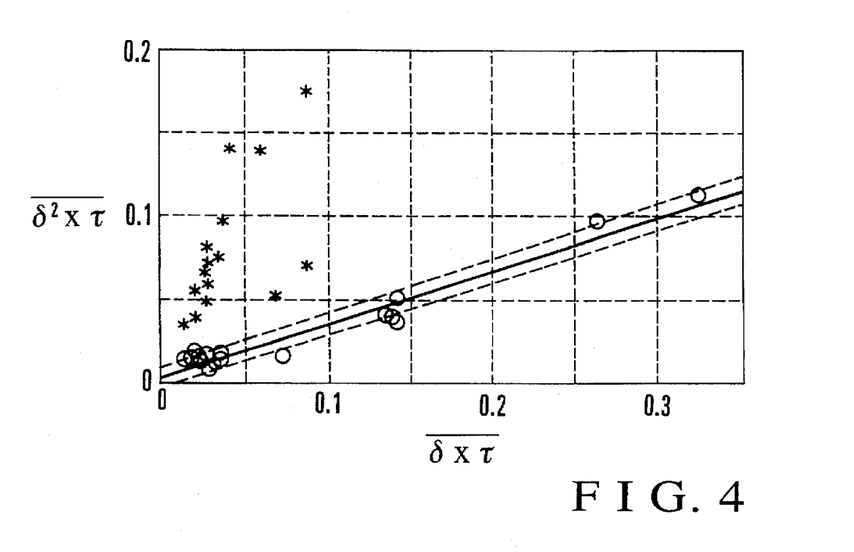
FIG. 4 is a graph showing the result obtained by measuring the state of the occurrence of stick-slip using a stick-slip detection apparatus according to the fourth embodiment of the present invention.

FIG. 4 show characteristics indicating the result obtained by measuring the state of the occurrence of stick-slip by using equations (16), (17), and (15). Referring to FIG. 4, the solid line represents a characteristic expression as a model obtained by a linear approximation of equation (15), and the two dotted lines indicate the range of errors $\pm\sigma$ in the model. This solid line indicates the state of the estimated second order difference values calculated from the first order difference values by using equation (15). Assume that a point is plotted at the coordinates indicated by the first and second order difference values calculated from the measurement values, the distance from the plotted point to the solid line indicates the difference $E\tau$ described above.

Referring to FIG. 4, "O" indicates the relationship between the first and second order difference values obtained by measurement in a normal state, whereas "*" indicates the relationship between the first and second order difference values obtained by measurement in a state in which stick-slip has occurred. That is, when the plot indicating the relationship between the first and second order difference values obtained by measurement greatly deviates from the range defined by the two dotted lines, it can be determined that stick-slip has occurred.

Fifth Embodiment

In the first to fourth embodiments described above, a second quantity of state is estimated from the first quantity of state calculated from a detected displacement signal by using a prepared relationship in a normal state, thereby calculating an estimated quantity of state. The difference between the calculated estimated quantity of state and the second quantity of state calculated from the displacement signal is obtained. However, the present invention is not limited to this. For example, a state in which stick-slip has occurred may be detected by comparing the prepared relationship in a normal state with the relationship between the first and second quantities of state obtained from the detected displacement signal.

Figure 5:
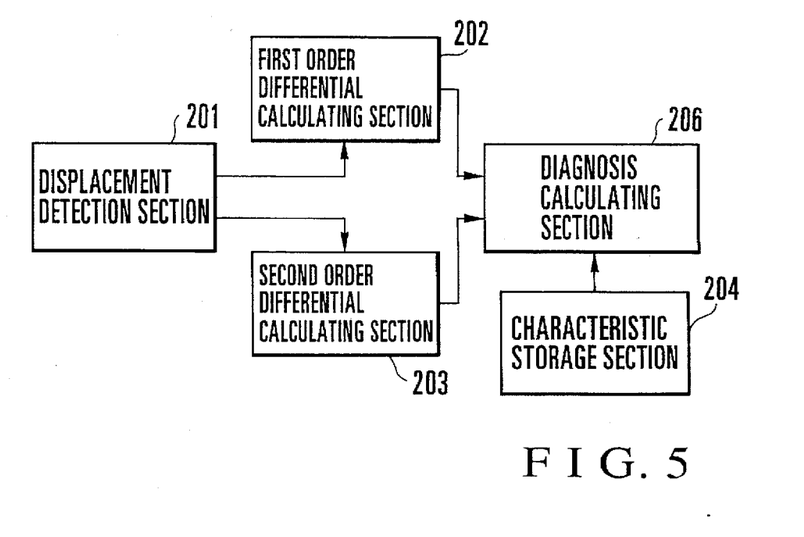
FIG. 5 is a block diagram showing the arrangement of a stick-slip detection apparatus according to the fifth embodiment of the present invention.

FIG. 5 shows the arrangement of a stick-slip detection apparatus according to the fifth embodiment of the present invention. As shown in FIG. 5, as in the first embodiment, a first order differential calculating section 202 calculates a first order differential value of a displacement as a first quantity of state from the displacement signal detected by a displacement detecting section 201. A second order differential calculating section 203 calculates a second order differential value of the displacement as a second quantity of state from the displacement detected by the displacement detecting section 201, as in the first embodiment.

The relationship between the first and second quantities of state in a normal state is stored in a characteristic storage section 204. A diagnosis calculating section 206 obtains the relationship between the first quantity of state calculated by the first order differential calculating section 202 and the second quantity of state calculated by the second order differential calculating section 203, and compares the obtained result with the relationship stored in the characteristic storage section 204, thereby detecting the occurrence of stick-slip.

In the fifth embodiment, a first order differential value of a detected displacement signal is used as a first quantity of state, and the second order differential value of the detected displacement signal is used as the second quantity of state. However, the present invention is not limited to this. For example, a first order difference value of a detected displacement signal may be used as a first quantity of state, and a second order difference value of the detected displacement signal may be used as a second quantity of state.

Sixth Embodiment

In the first to fifth embodiments described above, the equilibrium point of the power spectrum of the first order differential signal of the displacement of the slidable contact portion 43 is obtained, and the occurrence of stick-slip is detected on the basis of a change in the equilibrium point. However, the present invention is not limited to this. For example, the occurrence of stick-slip can be detected on the basis of the relationship between the average of the absolute values of the first order difference values of the displacement signal obtained from the piston 141 which is sliding back and forth and the average of the squares of the first order difference values.

Figure 6:
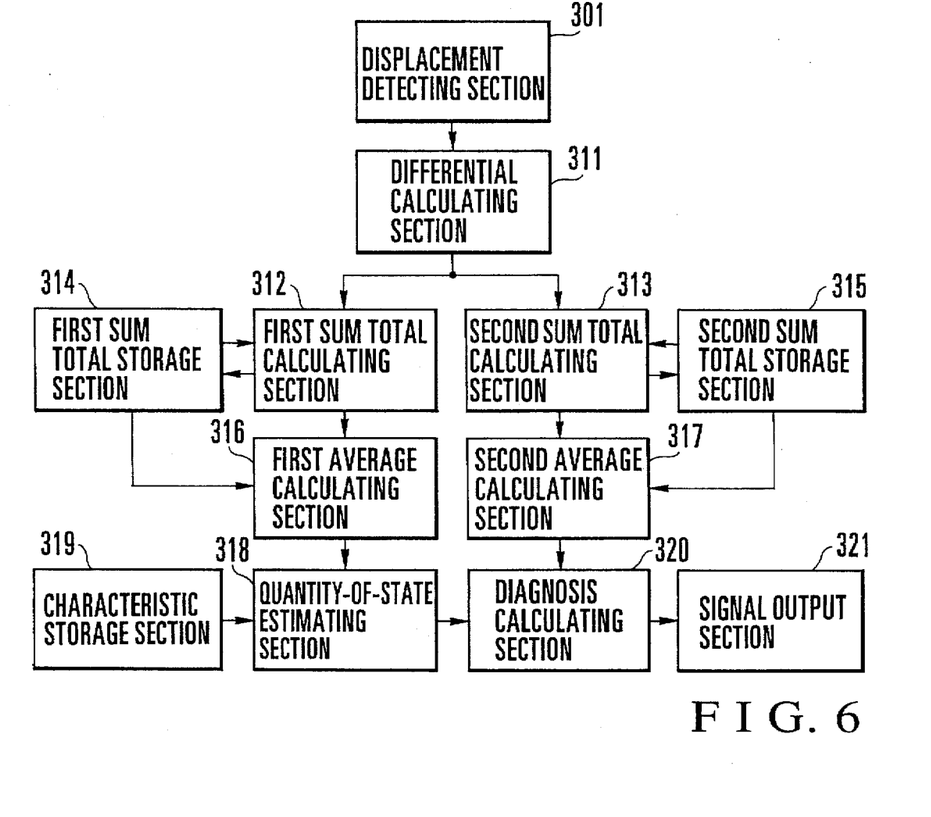
FIG. 6 is a block diagram showing the arrangement of a stick-slip detection apparatus according to the sixth embodiment of the present invention.

The sixth embodiment of the present invention will be described below with reference to FIG. 6. Referring to FIG. 6, a displacement detecting section 301 measures a displacement x of a piston 141 having a slidable contact portion 143 in FIG. 2 while a machine for which the occurrence of frictional vibrations is monitored is operating, and outputs a displacement signal. Upon reception of this displacement signal, a differential calculating section 311 obtains the first order difference values of the displacement signal in a time t. Note that a first order difference value δx is the difference between the values x in Δt1 and obtained by equation (18):

$$\delta x_\tau = x_{\tau + \Delta t1} - x_\tau \qquad (18)$$

Subsequently, a first sum total calculating section 312 adds the first order difference values obtained at time τ by the differential calculating section 311 to a sum $S_1'$ in a time interval $(m-1)\Delta t2$ which is stored in a first sum total storage section 314, thereby obtaining a sum $S_1$ of the first order difference values at time τ.

$$S_1 = S_1' + |\delta x_\tau| \qquad (19)$$

where $\delta x_\tau$ is the first order difference value at time τ.

Note that Δt2 represents the interval during which sum total calculation is executed. This sum total calculation execution interval Δt2 may be an equal interval. In the sixth embodiment, the sum total calculation execution interval Δt2 is an equal interval. In addition, m represents the number of times sum total calculation is executed, and the sum $S_1'$ stored in the first sum total storage section 314 is given by equation (20):

$$S_1' = \sum_{i=0}^{m-1} |\delta x_{\tau - m\Delta t2 + i\Delta t2}| \qquad (20)$$

The sum of the first order difference values, obtained by the first sum total calculating section 312, is stored in the first sum total storage section 314. At the same time, a second sum total calculating section 313 adds the squares of the first order difference values obtained at time τ by the differential calculating section 311 to a square sum $S_2'$ in $(m-1)\Delta t2$, stored in a second sum total storage section 315, thereby obtaining a square sum $S_2$ of the first order difference values at time τ, as indicated by equation (21):

$$S_2 = S_2' + (\delta x_\tau)^2 \qquad (21)$$

Note that the square sum $S_2'$ stored in the second sum total storage section 315 is given by equation (22):

$$S_2' = \sum_{i=0}^{m-1} (\delta x_{\tau - m\Delta t2 + i\Delta t2})^2 \qquad (22)$$

The square sum of the first order difference values obtained by the second sum total calculating section 313 is stored in the second sum total storage section 315.

When the number (m) of times sum total calculation is executed in the first sum total calculating section 312 and the second sum total calculating section 313 becomes a predetermined number N or more, or the sum total calculation execution time T=mΔt2 becomes a predetermined time T0 or more, the sum total calculation processing is complete. In the following description, the end of sum total calculation processing is determined on the basis of the predetermined number N of times.

When sum total calculation processing is complete, a first average calculating section 316 obtains a first quantity of state, which is the average of first order difference values of displacement, from the sum of first order difference values, stored in the first sum total storage section 314, and the number N of times sum total calculation is executed, according to equation (23) or (24):

$$|\overline{\delta x_\tau}|51 = \frac{1}{N+1} \sum_{i=0}^{N} |\delta x_{\tau - N\Delta t2 + i\Delta t2}| \qquad (23)$$

$$(\overline{|\delta x_\tau|})^2 = \left( \frac{1}{N+1} \sum_{i=0}^{N} |\delta x_{\tau - N\Delta t2 + i\Delta t2}| \right)^2 \qquad (24)$$

A second average calculating section 317 obtains a second quantity of state, which is the average of the squares of the first order difference values of displacement, from the square sum of the first order difference values, stored in the second sum total storage section 315, and the number N of times sum total calculation is executed, according to equation (25) or (26):

$$\sqrt{\overline{\delta x_\tau^2}} = \sqrt{\frac{1}{N+1} \sum_{i=0}^{N} (\delta x_{\tau-N\Delta t2+i\Delta t2})^2} \quad (25)$$

$$\overline{\delta x_\tau^2} = \frac{1}{N+1} \sum_{i=0}^{N} (\delta x_{\tau-N\Delta t2+i\Delta t2})^2 \quad (26)$$

When the first quantity of state is to be obtained by equation (23), the second quantity of state is obtained by equation (25). When the first quantity of state is to be obtained by equation (24), the second quantity of state is obtained by equation (26).

As described above, the first quantity of state is obtained by the first average calculating section 316, and the second quantity of state is obtained by the second average calculating section 317. A quantity-of-state estimating section 318 estimates a second quantity of state from the first quantity of state (average) obtained by measurement by using the relationship between the first and second quantities of state in a normal sliding state, which is stored in a characteristic storage section 319.

Estimation of the second state quantity in the quantity-of-state estimating section 318 will be described below. In the following description, the values obtained by equations (23) and (25) are used as the first and second quantities of state, respectively. As is apparent, equations (24) and (26) may be used instead of equations (23) and (25).

The relationship between the first quantity of state (average) and the second quantity of state (average of squares) in a normal sliding state, which is obtained by a linear approximation using a predetermined constant A as indicated by equation (27), is stored in the characteristic storage section 319. This relationship is prepared in advance.

$$\sqrt{\overline{\delta x^2}} = A \times |\overline{\delta x}| \quad (27)$$

where $|\overline{\delta x}|$ is the first quantity of state (average), and $\sqrt{\overline{\delta x^2}}$ is the second quantity of state (square average).

The quantity-of-state estimating section 318 estimates a second quantity of state by substituting the first quantity of state obtained by the first average calculating section 316 into equation (27) representing the normal sliding state and stored in the characteristic storage section 319, while a machine for which the occurrence of a friction signal is actually monitored is operating. A diagnosis calculating section 320 then compares this estimated second quantity of state with the actually measured second quantity of state which is obtained by the second average calculating section 317. In this comparing operation, the diagnosis calculating section 320 calculates the difference between the estimated second quantity of state and the actually measured second quantity of state according to equation (28):

difference $E_\tau$ = actual measurement value − estimated value

= $\sqrt{\overline{\delta x_\tau^2}} - (A \times |\overline{\delta x_\tau}|)$

If it is determined after the calculation according to equation (28) that the difference between the estimated second quantity of state and the actually measured second quantity of state is larger than a predetermined value, the diagnosis calculating section 320 determines that stick-slip has occurred. The determination result is output from a signal output section 321 to the outside. In the sixth embodiment, a second quantity of state is estimated. However, a first quantity of state may be estimated.

Seventh Embodiment

In the sixth embodiment described above, a second quantity of state is estimated. However, the relationship between the first and second quantities of state obtained by measurement may be compared with the relationship between the first and second quantities of state in a normal sliding state.

Figure 7:
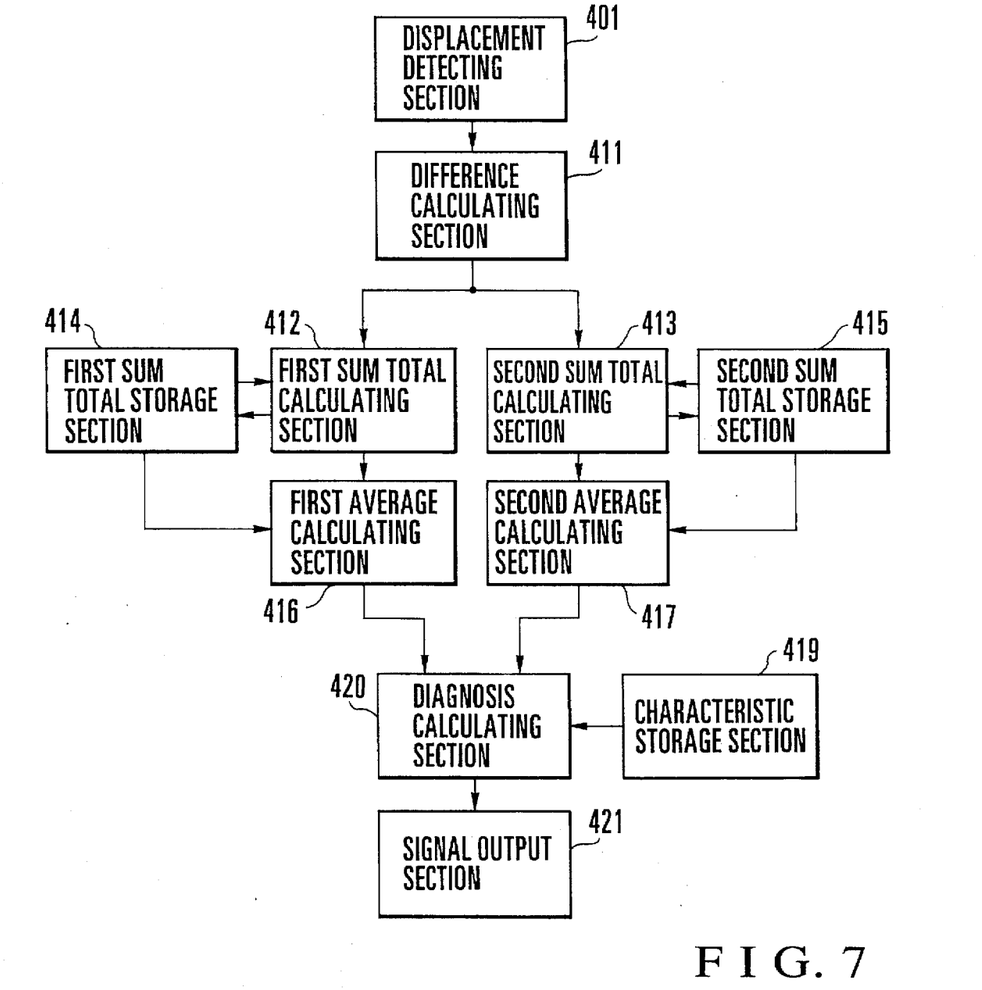
FIG. 7 is a block diagram showing the arrangement of a stick-slip detection apparatus according to the seventh embodiment of the present invention.

In the seventh embodiment, as shown in FIG. 7, a displacement detecting section 401 measures a displacement x of a piston 141 having a slidable contact portion 143 in FIG. 2 while a machine for which the occurrence of frictional vibrations is monitored is operating, and outputs a displacement signal. Upon reception of the displacement signal, a difference calculating section 411 obtains first order difference values of the displacement signal in a time t.

Subsequently, as in the sixth embodiment, a first sum total calculating section 412 adds the first order difference values obtained by the difference calculating section 411 at time τ to a sum $S_1'$ in a time interval (m−1)Δt2 which is stored in a first sum total storage section 414, thereby obtaining a sum $S_1$ of the first order difference values at time τ, as indicated by equation (19). The sum of the first order difference values, obtained by the first sum total calculating section 412, is stored in the first sum total storage section 414.

At the same time, a second sum total calculating section 413 adds the squares of the first order difference values obtained at time τ by the difference calculating section 411 to a square sum $S_2'$ in the time interval (m−1)Δt2 which is stored in a second sum total storage section 415, thereby obtaining a square sum $S_2$ of the first order difference values at time τ.

Upon completion of the sum total calculation processing, a first average calculating section 416 obtains a first quantity of state, which is the average of the first order difference values of the displacement, from the sum of the first order difference values, stored in the first sum total storage section 414, and the number (N) of times sum total calculation is executed. A second average calculating section 417 obtains a second quantity of state, which is the average of the squares of the first order difference values of displacement, from the square sum of the first order difference values, stored in the second sum total storage section 415, and the number N of times sum total calculation is executed.

As described above, the first quantity of state is obtained by the first average calculating section 416, and the second quantity of state is obtained by the second average calculating section 417. A diagnosis calculating section 420 obtains the relationship between the first and second quantities of state obtained by measurement, and compares it with the relationship between the first and second quantities of state obtained in the normal sliding state and stored in a characteristic storage section 419. The relationship between the first quantity of state (average) and the second quantity of state (average of squares) in the normal sliding state is stored in the characteristic storage section 419 by using a predetermined constant A, as indicated by equation (29):

$$\frac{\text{second quantity of state (average of squares)}}{\text{first quantity of state (average)}} = \frac{\sqrt{\overline{\delta x^2}}}{|\overline{\delta x}|} = A \quad (29)$$

where A is a constant.

The diagnosis calculating section 420 obtains the ratio (relationship) between the first quantity of state obtained by the first average calculating section 416 and the second quantity of state obtained by the second average calculating section 417 according to equation (30) while the machine for which the occurrence of frictional vibrations is monitored is operating.

$$\frac{\sqrt{\overline{\delta x_\tau^2}}}{\overline{\oplus \delta x_\tau}} = A_\tau \quad (30)$$

Subsequently, the diagnosis calculating section 420 compares the ratio obtained by equation (30) with a ratio A obtained in the normal sliding state and stored in the characteristic storage section 419 in the following manner. This comparing operation is performed by calculating the difference between the ratio obtained by equation (30) and the ratio A in the normal sliding state according to equation (31):

$$\text{difference } E_\tau = A_\tau - A$$

If the difference obtained by equation (31) becomes a predetermined value or more, the diagnosis calculating section 420 determines that stick-slip has occurred. The determination result is output from a signal output section 421 to the outside.

According to the seventh embodiment, the occurrence of stick-slip can be detected on the basis of the relationship between the average of the absolute values of the first order difference values, obtained by equation (23), and the square sum of the first order difference values, obtained by equation (25). Note that the relationship between the sum of the first order difference values and the square sum of the first order difference values can be used. In this case, however, in order to detect the occurrence of stick-slip, the respective values must be calculated values in the same time interval.

Figure 8A:
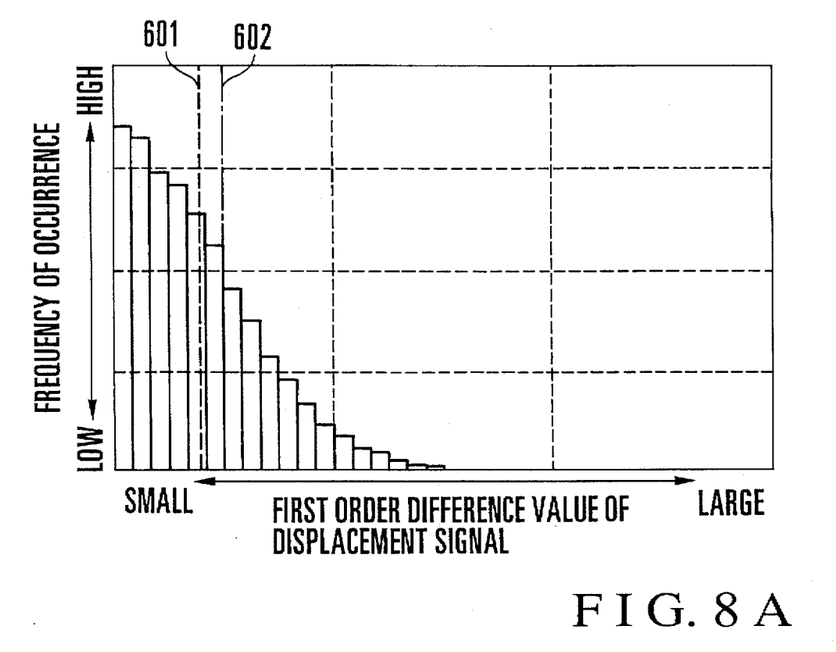
FIGS. 8A and 8B are histograms respectively showing the distributions of the frequencies of occurrence of the first order difference values of a displacement signal obtained from a movable member, which is sliding back and forth with and without stick-slip, in the stick-slip detection apparatus in FIG. 7.
Figure 8B:
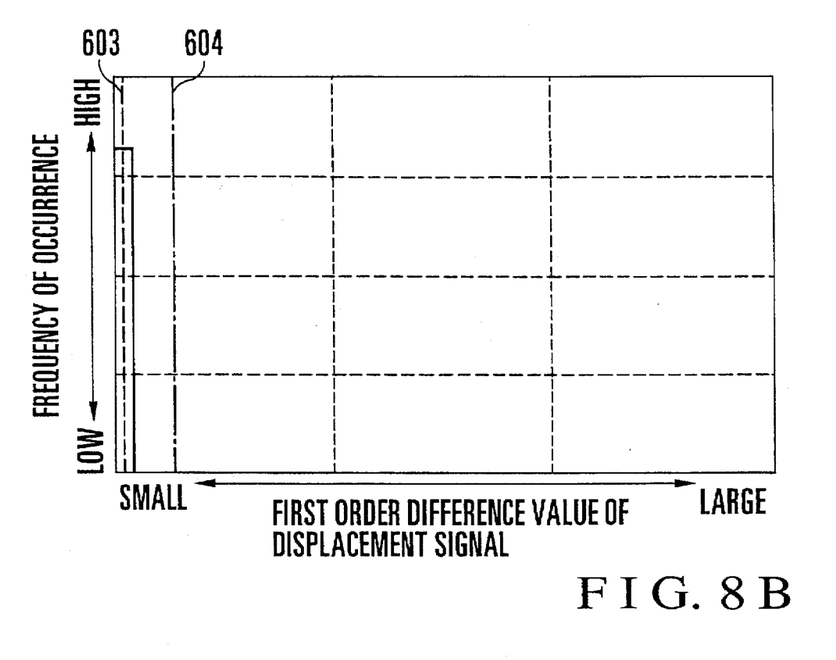

FIG. 8A shows the distribution of the frequencies of occurrence of the first order difference values of a displacement signal obtained from the piston 141 (FIG. 2) which is sliding back and forth in a normal sliding state. FIG. 8B shows the distribution of the frequencies of occurrence of the first order difference values of a displacement signal in a state in which stick-slip has occurred.

When no stick-slip has occurred, the difference between an average 601 of the absolute values of the first order difference values which is obtained by equation (23) and an average 602 of the squares of the first order difference values which is obtained by equation (25) is not so large, as shown in FIG. 8A. In contrast to this, when stick-slip has occurred, the difference between an average 603 of the absolute values of the first order difference values and an average 604 of the squares of the first order difference values becomes large, as shown in FIG. 8B. By monitoring changes in this difference, the occurrence of stick-slip can be detected.

Figure 9:
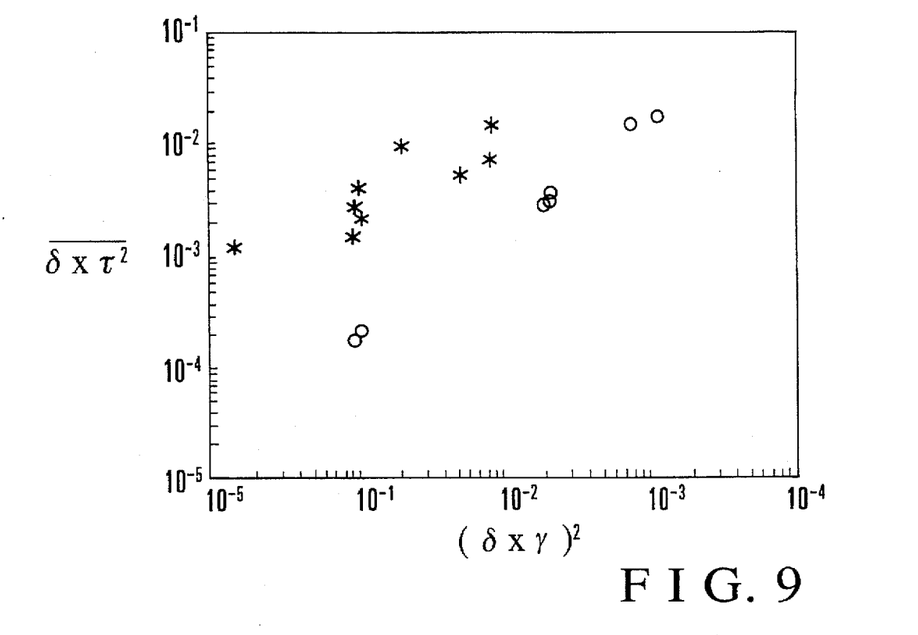
FIG. 9 is a graph showing the result obtained by measuring the state of the occurrence of stick-slip using the stick-slip detection apparatus in FIG. 7.

The result obtained by detecting the displacement of the piston 141 (FIG. 2) which is sliding back and forth is applied to the apparatus of the seventh embodiment. FIG. 9 shows the result of this application. Referring to FIG. 9, the abscissa represents the average of the absolute values of the first order difference values of the displacement signal obtained by detecting the displacement, i.e., the first quantity of state, and the ordinate represents the average of the squares of the first order difference values of the displacement signal obtained by detecting the displacement, i.e., the second quantity of state. In addition, referring to FIG. 9, "*" represents the value in the event of stick-slip; and "O", the value in a normal state.

As is apparent from FIG. 9, with the values in the normal state, an approximation like equation (29) can be performed. In contrast to this, the values in the event of stick-slip uniformly deviate from the approximation indicating the normal state. This is because the distribution of the frequencies of occurrence of relative speeds is skewed in the event of stick-slip as compared with the distribution in the normal state, and the average of the squares becomes large as compared with the average of the absolute values of the first order difference values.

In the first to seventh embodiments, each diagnosis calculating section calculates the difference. However, the section may obtain a ratio instead of the difference, and performs diagnosis by determining whether the ratio is larger than a predetermined value. Each embodiment described above is designed to detect stick-slip in the apparatus having the piston 141 with the slidable contact portion 143. However, the present invention can be applied to any apparatus having a movable member with a slidable contact portion. Furthermore, each embodiment described above is designed to detect stick-slip on the basis of the displacement of the piston 141 as a movable member with respect to the cylinder 142 as a stationary member. However, the present invention can also be applied to a case wherein stick-slip is detected on the basis of the relative displacement of two movable members.

Figure 12:
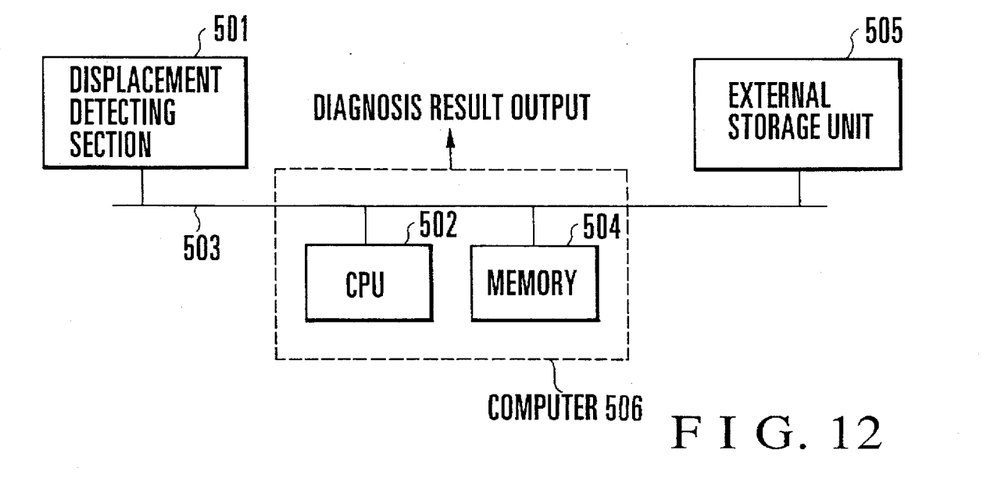
FIG. 12 is a block diagram showing the schematic arrangement of a stick-slip detection apparatus designed to process the detected displacement of a movable member by using a computer.

The above stick-slip detection can also be performed by processing a detected displacement using a computer. More specifically, as shown in FIG. 12, a CPU (Central Processing Unit) 502 of a computer 506 may process a displacement signal as a displacement detection result obtained by the displacement detecting section 501 to output the diagnosis result. The CPU 502 operates in accordance with the programs stored in a memory 504 connected to the CPU 502 through a bus 503. The programs stored in the memory 504 cause the computer 506 including the CPU 502 to perform the stick-slip detection processing in the first to fifth embodiments.

For example, the programs stored in the memory 504 cause the CPU 502 to perform operations corresponding to the functions of the first order differential calculating section 2, the second order differential calculating section 3, the second order differential value estimating section 5, and the diagnosis calculating section 6 in FIG. 2, and also include the description of the characteristic expression stored in the characteristic storage section 4. In this case, the CPU 502 loads information from an external storage unit 505 connected to the CPU 502 through the bus 503, and executes the programs stored in the memory 504. As the external storage unit 505, for example, a magnetic disk storage unit is available.

As has been described above, according to the present invention, the displacement of a movable member is accompanied by high-frequency components caused by stick-slip, and the difference between the quantity of state calculated from the displacement detected in accordance with the high-frequency components accompanying the displacement of the movable member and an estimated quantity of state changes. Since the difference between the two quantities of state is monitored in consideration of these phenomena, the occurrence of stick-slip can be detected. In addition, since the degree of the difference between a state in which stick-slip has occurred and a normal sliding state is expressed in quantity, the occurrence of stick-slip can be reliably detected.

In addition, when stick-slip has occurred, the frequency of the first order difference values, as the intermediate value, of the displacement of the movable member decreases. The relationship between the two quantities of state calculated on the basis of the displacement of the movable member changes in accordance with the presence/absence of stick-slip. Since the relationship between the two quantities of state is monitored in consideration of these phenomena, the occurrence of stick-slip can be detected. Furthermore, since the degree of the difference between a state in which stick-slip has occurred and a normal sliding state is expressed in quantity, the occurrence of stick-slip can be reliably detected.

What is claimed is:

1. A stick-slip detection method comprising the steps of:

detecting a displacement of a movable member having a slidable contact portion;

calculating a first quantity of state on the basis of the detected displacement of the movable member;

calculating a second quantity of state, which can be estimated from the first quantity of state, on the basis of the detected displacement of the movable member;

calculating an estimated quantity of state by estimating a second quantity of state from the calculated first quantity of state by using a relationship between first and second predetermined quantities of state which are obtained from a displacement of the movable member in a normal sliding state; and comparing the calculated second quantity of state with the estimated quantity of state, and determining an abnormal sliding operation of the movable member on the basis of the comparison result.

2. A method according to claim 1, wherein the step of calculating the first quantity of state comprises the step of detecting a small amount of change in the displacement of the movable member, and the step of calculating the second quantity of state comprises the step of detecting a small amount of change in the small amount of change in the displacement of the movable member.

3. A method according to claim 1, wherein the step of calculating the first quantity of state comprises the step of calculating an average of first order difference values of the displacement of the movable member, and the step of calculating the second quantity of state comprises the step of calculating an average of squares of the first order difference values of the displacement of the movable member.

4. A stick-slip detection method comprising the steps of:

detecting a displacement of a movable member having a slidable contact portion;

calculating a first quantity of state on the basis of the detected displacement of the movable member;

calculating a second quantity of state having a predetermined relationship with the first quantity of state on the basis of the detected displacement of the movable member; and comparing a relationship between the calculated first and second quantities of state with a relationship between first and second predetermined quantities of state which are obtained from a displacement of the movable member in a normal sliding state, and determining an abnormal sliding operation of the movable member on the basis of the comparison result.

5. A method according to claim 4, wherein the step of calculating the first quantity of state comprises the step of detecting a small amount of change in the displacement of the movable member, and the step of calculating the second quantity of state comprises the step of detecting a small amount of change in the small amount of change in the displacement of the movable member.

6. A method according to claim 4, wherein the step of calculating the first quantity of state comprises the step of calculating an average of first order difference values of the displacement of the movable member, and the step of calculating the second quantity of state comprises the step of calculating an average of squares of the first order difference values of the displacement of the movable member.

7. A stick-slip detection apparatus comprising:

displacement detecting means for detecting a displacement of a movable member having a slidable contact portion;

first calculating means for calculating a first quantity of state on the basis of the displacement of the movable member which is obtained by said displacement detecting means;

second calculating means for calculating a second quantity of state, which can be estimated from the first quantity of state, on the basis of the displacement of the movable member which is obtained by said displacement detecting means;

characteristic storage means in which a relationship between first and second quantities of state obtained from a displacement of the movable member in a normal sliding state is stored;

quantity-of-state estimating means for calculating an estimated quantity of state by estimating a second quantity of state from the first quantity of state obtained by said first calculating means by using the relationship in the normal sliding state which is stored in said characteristic storage means; and diagnosis calculating means for comparing the second quantity of state obtained by said second calculating means with the estimated quantity of state obtained by said quantity-of-state estimating means, and determining an abnormal sliding operation of the movable member on the basis of the comparison result.

8. An apparatus according to claim 7, wherein the first quantity of state calculated by said first calculating means is a small amount of change in the displacement of the movable member, and the second quantity of state calculated by said second calculating means is a small amount of change in the small amount of change in the displacement of the movable member.

9. An apparatus according to claim 7, wherein the first quantity of state calculated by said first calculating means is an average of first order difference values of the displacement of the movable member, and the second quantity of state calculated by said second calculating means is an average of squares of the first order difference values of the displacement of the movable member.

10. A stick-slip detection apparatus comprising:

displacement detecting means for detecting a displacement of a movable member having a slidable contact portion;

first calculating means for calculating a first quantity of state on the basis of the displacement of the movable member which is obtained by said displacement detecting means;

second calculating means for calculating a second quantity of state having a predetermined relationship with the first quantity of state on the basis of the displacement of the movable member which is obtained by said displacement detecting means;

characteristic storage means in which a relationship between first and second quantities of state obtained from a displacement of the movable member in a normal sliding state is stored; and diagnosis calculating means for comparing a relationship between the first quantity of state obtained by said first calculating means and the second quantity of state obtained by said second calculating means with the relationship in the normal sliding state which is stored in said characteristic storage means, and determining an abnormal sliding operation of the movable member on the basis of the comparison result.

11. An apparatus according to claim 10, wherein the first quantity of state calculated by said first calculating means is a small amount of change in the displacement of the movable member, and the second quantity of state calculated by said second calculating means is a small amount of change in the small amount of change in the displacement of the movable member.

12. An apparatus according to claim 10, wherein the first quantity of state calculated by said first calculating means is an average of first order difference values of the displacement of the movable member, and the second quantity of state calculated by said second calculating means is an average of squares of the first order difference values of the displacement of the movable member.

13. A stick-slip detection apparatus comprising:

displacement detecting means for detecting a displacement of a movable member having a slidable contact portion;

difference calculating means for calculating first order difference values of the displacement of the movable member which is obtained by said displacement detecting means;

first sum total calculating means for calculating a sum of the first order difference values obtained by said difference calculating means;

first average calculating means for calculating a first quantity of state from an average of at least part of the sum of the first order difference values which is obtained by said first sum total calculating means;

second sum total calculating means for calculating a square sum of the first order difference values obtained by said difference calculating means;

second average calculating means for calculating a second quantity of state from an average of at least part of the square sum of the first order difference values which is obtained by said second sum total calculating means;

characteristic storage means in which a relationship between first and second quantities of state which are obtained from a displacement of the movable member in a normal sliding state is stored;

quantity-of-state estimating means for calculating an estimated quantity of state by estimating a second quantity of state from the first quantity of state obtained by said first average calculating means by using the relationship in the normal sliding state which is stored in said characteristic storage means; and diagnosis calculating means for comparing the second quantity of state obtained by said second average calculating means with the estimated quantity of state obtained by said quantity-of-state estimating means, and determining an abnormal sliding operation of the movable member on the basis of the comparison result.

14. A stick-slip detection apparatus comprising:

displacement detecting means for detecting a displacement of a movable member having a slidable contact portion;

difference calculating means for calculating first order difference values of the displacement of the movable member which is obtained by said displacement detecting means;

first sum total calculating means for calculating a sum of the first order difference values obtained by said difference calculating means;

first average calculating means for calculating a first quantity of state from an average of at least part of the sum of the first order difference values which is obtained by said first sum total calculating means;

second sum total calculating means for calculating a square sum of the first order difference values obtained by said difference calculating means;

second average calculating means for calculating a second quantity of state from an average of at least part of the square sum of the first order difference values which is obtained by said second sum total calculating means;

characteristic storage means in which a relationship between first and second quantities of state which are obtained from a displacement of the movable member in a normal sliding state is stored; and diagnosis calculating means for comparing a relationship between the first quantity of state obtained by said first average calculating means and the second quantity of state obtained by said second average calculating means with the relationship in the normal sliding state which is stored in said characteristic storage means.

* * * * *